United States Patent [19]

Pettersson et al.

[11] Patent Number: 6,136,292

[45] Date of Patent: Oct. 24, 2000

[54] DETERMINATION OF NON-FUNCTIONING AREAS OF THE G.I. TRACT USING MRI OF MANGANESE COMPOSITION

[75] Inventors: Göran Pettersson, Hjärup, Sweden; Klaes Golman, Rungsted Kyst, Denmark; Anne Jacobsen, Baerums Verk, Norway; Liv-Ingrid Ødegårdstuen, Leirsund, Norway; Anne Kjersti Fahlvik, Oslo, Norway

[73] Assignee: Nycomed Imaging AS, Oslo, Norway

[21] Appl. No.: 09/078,720

[22] Filed: May 14, 1998

Related U.S. Application Data

[63] Continuation of application No. PCT/GB97/02073, Jul. 30, 1997.
[60] Provisional application No. 60/046,648, May 16, 1997.

[30] Foreign Application Priority Data

Sep. 23, 1996 [GB] United Kingdom .................... 9619758

[51] Int. Cl.[7] ...................................... A61B 5/055
[52] U.S. Cl. ...................... 424/9.36; 424/9.3; 424/9.322; 514/836
[58] Field of Search ...................... 424/9.36, 9.3, 424/9.322, 9.42; 514/836; 600/420

[56] References Cited

U.S. PATENT DOCUMENTS

| | | | |
|---|---|---|---|
| 4,915,933 | 4/1990 | Matwiyoff | 424/9 |
| 5,248,492 | 9/1993 | Groman et al. | 424/9 |
| 5,314,681 | 5/1994 | Leunbach et al. | 424/9 |
| 5,358,702 | 10/1994 | Unger | 424/9 |
| 5,401,492 | 3/1995 | Kellar et al. | 424/9 |
| 5,515,863 | 5/1996 | Damadian | 128/653.4 |
| 5,534,240 | 7/1996 | Hasegawa et al. | 424/9.36 |
| 5,658,550 | 8/1997 | Unger | 424/9.36 |
| 5,716,598 | 2/1998 | Golman et al. | 424/9.36 |
| 5,738,837 | 4/1998 | Klaveness et al. | 424/9.36 |
| 5,863,519 | 1/1999 | Golman et al. | 424/9.36 |
| 5,869,023 | 2/1999 | Ericcson et al. | 424/9.36 |
| 5,922,304 | 7/1999 | Unger | 424/9.3 |

FOREIGN PATENT DOCUMENTS

| | | |
|---|---|---|
| WO 95/02831 | 1/1995 | WIPO . |
| WO 96/05867 | 2/1996 | WIPO . |
| WO 97/02842 | 1/1997 | WIPO . |

OTHER PUBLICATIONS

D'Agincourt, L., "MRI Agents for Abdomen Offer High Sensitivity", Diagnostic Imaging International, vol. 8, No. 6, Sep. 1, 1992, pp. 42–43, 45, 47–50.

*Primary Examiner*—Gary E. Hollinden
*Attorney, Agent, or Firm*—Bacon & Thomas

[57] ABSTRACT

The invention provides a method of functional imaging of a human or non-human animal body, which method comprises administering into the gastrointestinal tract of a said body an effective amount of a composition comprising (a) a first contrast agent comprising a physiologically tolerable manganese compound or a salt thereof, together with (b) a second contrast agent, and generating a functional image of the gastrointestinal tract of said body.

This imaging technique has surprisingly been found to provide clear delineation of those portions of the gut wall in which manganese uptake is occurring, thereby enabling not only the detection of tumors in the gut, but also the identification of regions of the gut which may be functioning abnormally.

24 Claims, 4 Drawing Sheets

DETERMINATION OF NON-FUNCTIONING AREAS OF THE G.I. TRACT USING MRI OF MANGANESE COMPOSITION

This application claims the benefit of US Provisional Application No. 60/046648 filed May 16, 1997 and is a continuation of the US designation of PCT/GB97/02073 filed Jul. 30, 1997.

FIELD OF THE INVENTION

The present invention relates to improvements in and relating to magnetic resonance imaging (MRI), in particular to the use of manganese compounds in the preparation of contrast media for imaging of the gastrointestinal tract.

BACKGROUND OF THE INVENTION

MRI is now well established as a medical diagnostic tool. The ability of the technique to generate high quality images and to differentiate between soft tissues without requiring the patient to be exposed to ionizing radiation has contributed to this success.

Although MRI can be performed without using added contrast media, it has been found that substances which affect the nuclear spin reequilibration of the nuclei (hereinafter the "imaging nuclei"—generally water protons in body fluids and tissues) responsible for the magnetic resonance (MR) signals from which the images are generated may be used to enhance image contrast and, accordingly, in recent years, many such materials have been suggested as MRI contrast agents.

The enhanced contrast obtained with the use of contrast agents enables particular organs or tissues to be visualized more clearly by increasing or by decreasing the signal level of the particular organ or tissue relative to that of its surroundings. Contrast agents raising the signal level of the target site relative to that of its surroundings are termed "positive" contrast agents whilst those lowering the signal level relative to surroundings are termed "negative" contrast agents.

The majority of materials now being proposed as MRI contrast media achieve a contrast effect because they contain paramagnetic, superparamagnetic or ferromagnetic species.

Paramagnetic contrast agents may be either positive or negative MRI contrast agents. The effect of paramagnetic substances on magnetic resonance signal intensities is dependent on many factors, the most important of which are the concentration of the paramagnetic substance at the imaged site, the nature of the paramagnetic substance itself and the pulse sequence and magnetic field strength used in the imaging routine. Generally, however, paramagnetic contrast agents are positive MRI contrast agents at low concentrations where their $T_1$ lowering effect dominates and negative MRI contrast agents at higher concentrations where their $T_2$ (or $T_2^*$) lowering effect is dominant.

An example of a physiologically tolerable paramagnetic material known for use as an MRI contrast agent is manganese ion, which may conveniently be used in the form of its salts or chelates.

Manganese, when administered intravenously as a contrast agent, may be teratogenic at clinical dosages. Administered intravenously, manganese is also known to interfere with the normal functioning of the heart by replacement of calcium in the calcium pump of the heart.

In order to reduce the direct effect on the heart, oral administration of manganese has been proposed. A result of the vascularisation of the upper gastrointestinal tract is that orally administered material taken up into the blood from the gut passes to the liver before passing to the heart. In the case of manganese, absorption by the hepatocytes in the liver prevents cardiotoxic levels of manganese reaching the heart. This hepatocyte uptake of manganese has led to the use of orally administered manganese as a liver imaging contrast agent.

However, development of MRI as a technique for imaging the gastrointestinal (g.i.) tract has been hindered by problems particular to the g.i. tract in which natural inter-tissue contrast is relatively poor and in the absence of a particularly effective contrast medium.

U.S. Pat. No. 5,143,716 concerns methods of imaging of the gastrointestinal region to detect the presence of tumorous tissue. The contrast medium described comprises a combination of at least one polyphosphorylated compound and at least one paramagnetic ion, including $Mn^{2+}$. Whilst it is suggested that such a contrast medium is capable of providing images showing any diseased tissue in the g.i. tract, this does not permit the detection of regions of the gut, in particular the gut wall, which may be functioning abnormally.

SUMMARY OF THE INVENTION

It has now surprisingly been found that particularly enhanced images of the g.i. tract may be obtained through the combined use of manganese with a second contrast agent, preferably one which is retained within the gut and there exhibits a negative contrast effect. In particular, it has been found that such a combination of contrast agents enables visualisation of the structure and functioning of the gut wall thereby enabling discrimination between functioning and non-functioning regions of the intestine.

Thus viewed from one aspect the invention provides a method of functional imaging of a human or non-human, preferably mammalian, animal body, which method comprises administering into the gastrointestinal tract of a said body an effective amount of a composition comprising (a) a first contrast agent comprising a physiologically tolerable manganese compound or a salt thereof, together with (b) a second contrast agent, preferably one capable with said first agent of achieving negative contrast in the gastrointestinal tract, and generating a functional image of the gastrointestinal tract of said body. Conveniently, the composition for use in accordance with the method of the invention is enterally, e.g. orally or rectally, administered.

By functional imaging it is meant that the imaging technique provides clear delineation of those portions of the gut wall in which manganese uptake is occurring. Thus, the method in accordance with the invention not only enables the detection of tumors within the gut, but also enables the identification of regions of the gut which may be functioning abnormally, for example areas which may be the site of infection or areas in which the gut wall may be damaged or diseased.

The manganese may conveniently be administered as a combined preparation with the second contrast agent. Alternatively, the second contrast agent may be administered separately, prior to, during or subsequent to administration of the manganese-containing contrast medium.

Viewed from a further aspect the invention thus provides a method of functional imaging of a human or non-human, preferably mammalian, animal body, which method comprises simultaneous, separate or sequential administration into the gastrointestinal tract of a said body an effective amount of (a) a physiologically tolerable manganese compound, or a salt thereof, and (b) a second contrast agent, and generating a functional image of the gastrointestinal tract of said body.

Viewed from another aspect the invention also provides an MRI contrast agent kit comprising a physiologically tolerable manganese compound, or a salt thereof, and separately a second contrast agent for simultaneous, separate or sequential administration in a method of functional imaging of the gastrointestinal tract of a human or non-human animal body.

The kit in accordance with the invention may be used for the separate administration of the contrast agents or, alternatively, the contrast agents from the kit may be mixed and administered together.

DETAILED DESCRIPTION

Figure 1:
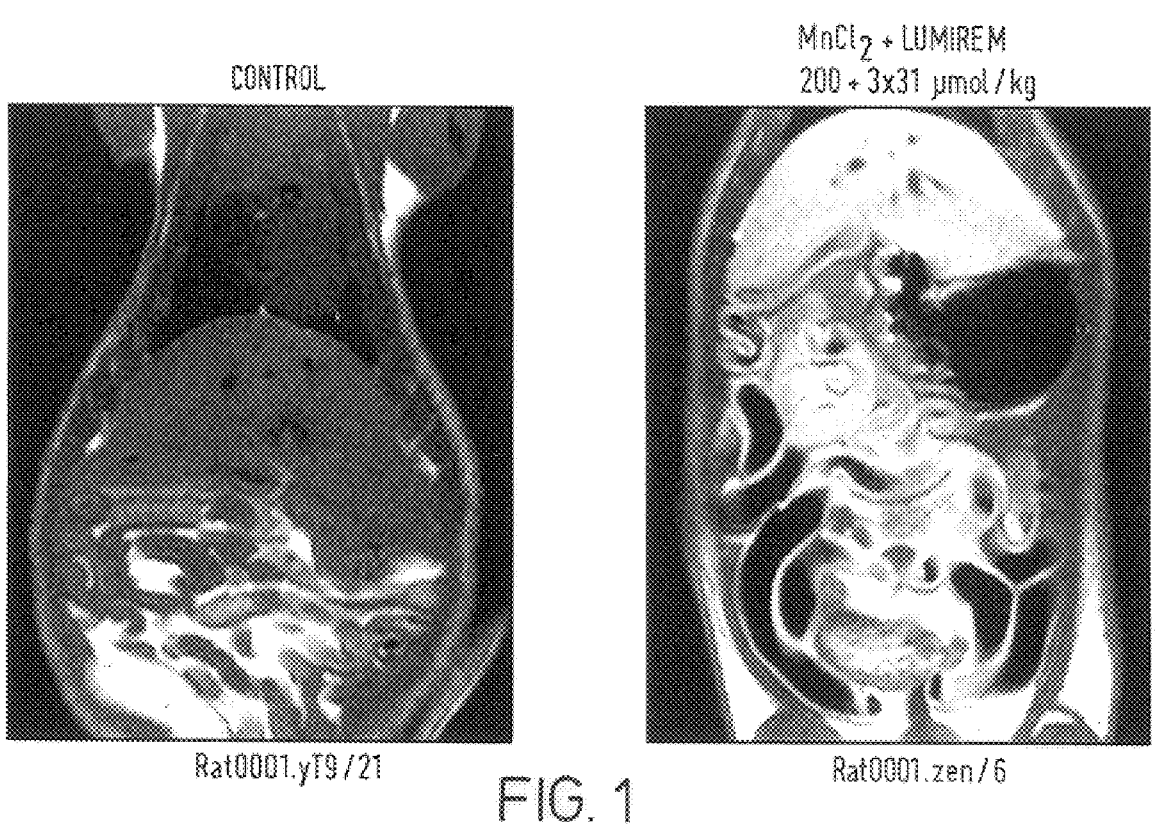
FIG. 1 illustrates the effect of orally administered $MnCl_2$+Lumirem®.

As mentioned above, paramagnetic materials such as manganese ions may act as either positive or negative MRI contrast agents depending upon a number of factors, including the concentration of the ions at the imaging site and the magnetic field strength used in the imaging procedure. Depending upon the resulting manganese ion concentration within the g.i. tract, this may be such as to create a signal suppressing or enhancing effect there.

In general, at the concentrations contemplated for use in accordance with the invention the manganese-containing contrast agent will function outside the gut contents as a positive contrast agent. The second contrast agent is therefore conveniently a negative contrast agent and may be any negative MRI contrast agent suitable for enteral administration.

Examples of negative MRI contrast agents for use in accordance with the method of the invention include known ferromagnetic and superparamagnetic species, e.g. AMI 227, SINEREM from Advanced Magnetics, and for example magnetic iron oxide particles either free or enclosed within or bound to a non-magnetic matrix material such as the magnetic polymer particles available under the trade names LUMIREM (Guerbet SA) and ABDOSCAN (Nycomed Imaging AS).

Further examples of a second contrast agent for use in accordance with the method of the invention include Gd and Dy ions bound to a polymeric matrix, for example the materials available under the trade name GADOLITE (Gadolinium alumina silicate oral suspension), available from Pharmacyclics. Yet further examples include known susceptibility agents such as insoluble barium compounds, e.g. barium sulphate, and other agents commonly used in barium meals or barium enemas in X-ray investigations of the gut.

Other examples of negative contrast agents suitable for use in accordance with the invention include gases, gas generating agents or gas filled particles. Thus, the second contrast agent may comprise a gas generating agent capable of releasing a gas, such as $CO_2$ or $N_2$, following oral administration. Preferred gas generating agents are those capable of releasing $CO_2$ or $N_2$ on contact with the gastric juices in the stomach. Alternatively, if delayed release of the gas is desirable, this can be achieved by providing the gas generating agent with a coating which does not dissolve on contact with the gastric juices. Examples of suitable gas generating agents for use in accordance with the invention include $MnCO_3$, $Na_2CO_3$ and $NaHCO_3$.

The manganese compound, which for oral administration is preferably soluble in gastrointestinal fluid may for example be a chelate or a salt, or may be a mixture of different salts and/or chelates. Particularly preferred are metal chelates and salts in which the manganese is present as Mn(II) rather than Mn(III) since the former has a higher magnetic moment and thus is more effective as an MR contrast agent.

Examples of manganese compounds particularly suitable for use in accordance with the invention include manganese chloride, ascorbate, kojate, salicylate and gluconate.

Diagnostically effective levels of uptake of manganese may conveniently be achieved by ensuring that no food or hydrophilic polymer components containing a significant amount of a $Mn^{2+}$-chelating unit are simultaneously present in the gut, e.g. by administering the manganese compound following a period of fasting. By "significant amount" is meant that the amount of $Mn^{2+}$-chelating unit is sufficiently high so as to influence the uptake of manganese.

Thus, conveniently, the manganese compound is itself substantially free from hydrophilic polymer components containing a significant amount of a $Mn^{2+}$-chelating unit and is administered to a human or non-human animal body which has fasted for a period of at least 6, preferably at least 10, more preferably at least 12 hours before enteral administration of the manganese composition.

By fasting it is meant that no solid food which may contain hydrophilic polymer components containing a significant amount of a $Mn^{2+}$-chelating unit, in particular soluble or fibrous hydrophilic polymers, has been consumed within the stated period. Water or sugar containing fluids may be taken during the fasting period.

In one embodiment the invention provides a method of obtaining enhanced images of the liver and the lower gut by means of rectal administration of the contrast medium. Due to the vascularisation of the lower gut, rectally administered manganese passes directly to the heart following absorption, without first passing through the liver. We have, however, surprisingly found that effective uptake of manganese in the lower gut can be achieved using lower doses of rectally administered manganese, resulting in particularly enhanced images of the lower gut. This is of particular value in detecting tumours in the lower gut, e.g. in the diagnosis of colorectal cancer.

Conveniently, the contrast agents are rectally administered to the g.i. tract of a human or non-human animal body which is substantially free from hydrophilic polymer components containing a significant amount of a $Mn^{2+}$-chelating unit at the time of imaging. Thus, for example, the contrast agents may be administered to a human or non-human animal body which has fasted for a period of at least 6, preferably at least 10, more preferably at least 12 hours.

Maximum uptake of the rectally administered contrast agents may, however, be achieved by prior irrigation of the colon, thereby ensuring that this is substantially free from any hydrophilic polymer components containing a significant amount of a $Mn^{2+}$-chelating unit.

Rectal administration may be via rectally inserted tubes which enable administration of the contrast medium to a selected region of the gut. Rectal administration may be advantageous and is known to introduce less nausea than a similar dose administered orally.

In a preferred embodiment of the invention, rectal administration of the manganese contrast agent may be combined with insufflation of the lower g.i. tract to obtain a particularly enhanced double contrast effect. Insufflation may conveniently be achieved by blowing a gas, such as air, preferably $CO_2$ or $N_2$, into the lower colon either simultaneously or subsequent to administration of the manganese contrast agent. In this way, the bulk of the lower colon is filled with gas and the manganese contrast agent is present inside and in connection with the walls of the gut. In the resulting MR images, the bulk of the colon is blackened out and the gut walls are highlighted.

The manganese compounds may conveniently be used in combination with one or more uptake promoters capable of enhancing manganese transport across the membranes of the g.i. tract. Examples of such uptake promoters are described in WO-A-96/05867. Alternatively, the manganese compound is administered substantially free from such uptake promoter.

Suitable uptake promoters include reducing compounds containing an α-hydroxy ketone group (—CH(OH)—CO—), acids containing α- and/or β-hydroxy or amino groups, vitamin D and mixtures thereof. The reducing nature of the uptake promoter is important since normal uptake of manganese by the gut tends to favour Mn(II) rather than Mn(III).

As used herein, the expression "acids containing α- and/or β-hydroxy or amino groups" is intended to include aromatic acids containing ortho-hydroxy or ortho-amino groups.

Preferred uptake promoters include those in which the reducing compound further contains an oxygen atom in a heterocyclic ring structure.

Particularly preferred as uptake promoters are ascorbic and kojic acids. Ascorbic acid has been found to increase the uptake of manganese in the g.i. tract about 5-fold compared with oral administration of $MnCl_2$ alone. Moreover, ascorbic acid (vitamin C) is cheap, readily available and particularly well tolerated by the body. When administered orally, it also serves to mask the metallic taste of the manganese, thus improving the taste of the contrast medium.

Examples of acids which have been found to be particularly effective as uptake promoters include carboxylic acids, e.g. gluconic and salicylic acid. α- and β-amino acids have also been found to be useful as uptake promoters, in particular α-amino acids, e.g. alanine, glycine, valine, glutamine, aspartic acid, glutamic acid, lysine, arginine, cysteine and methionine, especially arginine, lysine and aspartic acid.

Conveniently, the molar ratio of manganese to uptake promoter is from 1:0.2 to 1:50, e.g. 1:1 to 1:20, particularly 1:1 to 1:10, more preferably 1:1 to 1:8, yet more preferably 1:1 to 1:6, especially 1:2 to 1:6, particularly preferably about 1:5.

Alternatively, the molar ratio of manganese to uptake promoter may be in the range of from 1:1.5 to 1:5, e.g. 1:1.5 to 1:4, particularly 1:2 to 1:4, especially 1:2 to 1:3, particularly preferably about 1:2.

The uptake promoter may if desired be present in whole or in part as the counterion to the manganese ions. Thus in one embodiment the manganese compound for use in accordance with the invention comprises a manganese salt of a reducing compound containing an α-hydroxy ketone group, or a manganese salt of an acid containing α- and/or β-hydroxy or amino groups, e.g. manganese (II) ascorbate or manganese salicylate.

Whilst a broad range of manganese concentrations is deemed to fall within the scope of the invention, there will generally be two preferred concentration ranges—one enabling strong negative contrast to be obtained between the intestine and the surrounding muscle tissue and the other providing strong positive contrast. For negative contrast the concentration of manganese is conveniently greater than 10 mM, preferably in the range of from 10 mM to 50 mM. For positive contrast the manganese concentration is conveniently in the range of from 0.1 mM to 10 mM, preferably from 1 mM to 6 mM.

Since the manganese is also present in the g.i. tract, the quantity of the second contrast agent necessary to achieve negative contrast within the gut may be significantly lower, e.g. ⅕ to ½ the quantity required in the absence of the manganese.

When using the contrast media to obtain images of the gut, in order to avoid image artefacts resulting from pockets of the gut being contrast agent free, it is desirable to incorporate in the contrast media a viscosity enhancing agent which attains its full viscosity enhancing effect only after administration of the contrast medium. The contrast medium is thus able to be ingested in a relatively tolerable form while yet developing the desired viscosity at or during passage towards the site which is to be imaged. Examples of suitable viscosity enhancers are described in WO-A-91/01147 and WO-A-91/01148.

One of the problems encountered in imaging of the g.i. tract is that the MR signal intensity has a tendency to vary due to physical movements in the region being imaged. This problem can to some extent be overcome by the use of fast imaging procedures. Techniques capable of generating images with time intervals of less than 20 seconds (thus enabling imaging during one single "breath hold") are preferred for use in accordance with the method of the invention. Particularly suitable techniques include spin echo procedures (TR=80–150 ms, TE=10–14 ms) and gradient echo procedures (TR≈50 ms, TE=4 ms, flip angle=80–90°). The gradient echo sequence should preferably be spoiled.

The contrast agent compositions for use in the invention are particularly suited to use, if required after dispersion in aqueous media, for imaging of the stomach, intestine, bile duct and gall bladder. For such a purpose the contrast media may be administered into the gastrointestinal tract orally, rectally or via a tube inserted orally or rectally.

It has been shown in animal experiments that oral administration of Mn ascorbate and of iron oxide particles bound to a polymeric matrix results in the production of greatly improved MR images of the gastrointestinal system. Not only was imaging of the intestine enhanced, but it was also possible to observe the functioning and structure of the wall of the intestine. Thus the combination of MRI contrast agents in accordance with the invention allows in vivo imaging of the functioning and structure of the g.i. tract, in particular of the wall of the gut to an extent not previously observed. In this way, the method of the invention may permit discrimination between functioning and non-functioning regions of the intestinal tract.

The method of imaging in accordance with the invention also provides enhanced imaging of the abdomen as a whole, in particular the liver.

In the method of the invention the imaging technique used in preferably a spiral MR technique, equivalent to spiral CT techniques, which permits generation of an image corresponding to an internal (or external) transit along the gut. In such a technique, differences in manganese uptake by the gut wall due to localised malfunctions of the gut wall are readily visualised. Thus, differences in signal intensity from different regions of the gut wall can provide an indication of functioning and non-functioning areas of the gut.

The method of the invention thus may conveniently be used to generate a series of images through the g.i. tract, resulting in the production of high quality 3D images. This effectively allows the radiologist to obtain a view through the inside of the intestinal tract.

The contrast medium compositions for use in accordance with the invention may include other components, for example conventional pharmaceutical formulation aids such as wetting agents, buffers, disintegrants, binders, fillers, flavouring agents and liquid carrier media such as sterile water, water/ethanol etc.

For oral administration, the pH of the composition is preferably in the acid range, eg. 2 to 7 and while any uptake promoter present may itself serve to yield a composition with this pH, buffers or pH adjusting agents may be used.

The contrast media may be formulated in conventional pharmaceutical administration forms, such as tablets, capsules, powders, solutions, dispersions, syrups, suppositories etc.

The preferred dosage of the contrast media will vary according to a number of factors, such as the administration route, the age, weight and species of the subject and, if present, the particular uptake promoter used. Conveniently, the dosage of manganese may be in the range of from 2–400 times the normal recommended daily dose of manganese, e.g. from 5 to 500 μmol/kg bodyweight, preferably from 5 to 150 μmol/kg bodyweight, more preferably from 10 to 100 μmol/kg bodyweight, while the dosage of the uptake promoter, if present, may be in the range of from 5 μmol to 1 mmol/kg bodyweight, preferably from 25 μmol to 0.5 mmol/kg bodyweight.

Embodiments of the invention will now be further described by way of illustration and with reference to the accompanying figures, in which:

FIG. 1 illustrates the effect of orally administered $MnCl_2$ (200 μmol/kg)+Lumirem® (93 μmol Fe/kg) on signal intensity of coronal $T_1$-weighted spin-echo images (TR/TE=120/12 ms) 2 hours after administration in fasted (18 hours) rats. Lumirem® was administered three times, at 0, 30 and 60 min after administration of $MnCl_2$. The strong enhancement of the signal intensity of the liver and the intestinal wall is to be noted.

Figure 2:
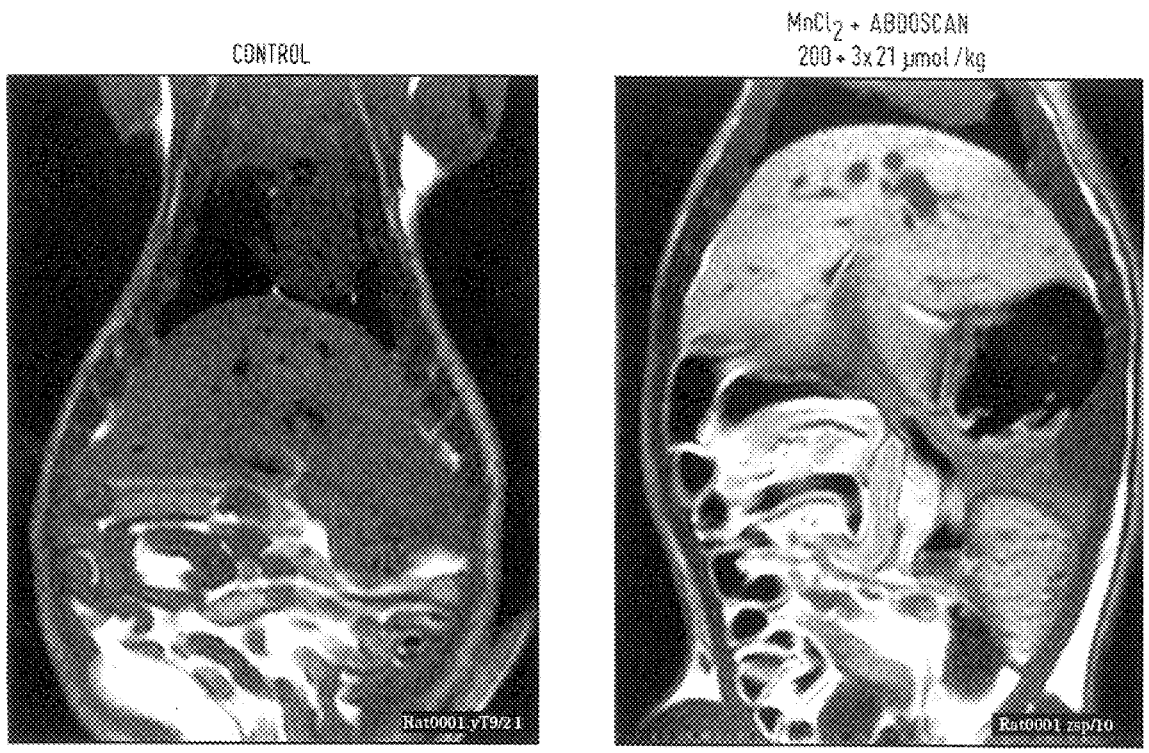
FIG. 2 illustrates the effect of orally administered $MnCl_2$+Abdoscan®.

FIG. 2 illustrates the effect of orally administered $MnCl_2$ (200 μmol/kg)+Abdoscan® (63 μmol Fe/kg) on signal intensity of coronal $T_1$-weighted spin-echo images (TR/TE=120/12 ms) 2 hours after administration in fasted (18 hours) rats. Abdoscan® was administered three times, at 0, 30 and 60 min after administration of $MnCl_2$. The strong enhancement of the signal intensity of the liver and the intestinal wall is to be noted.

Figure 3:
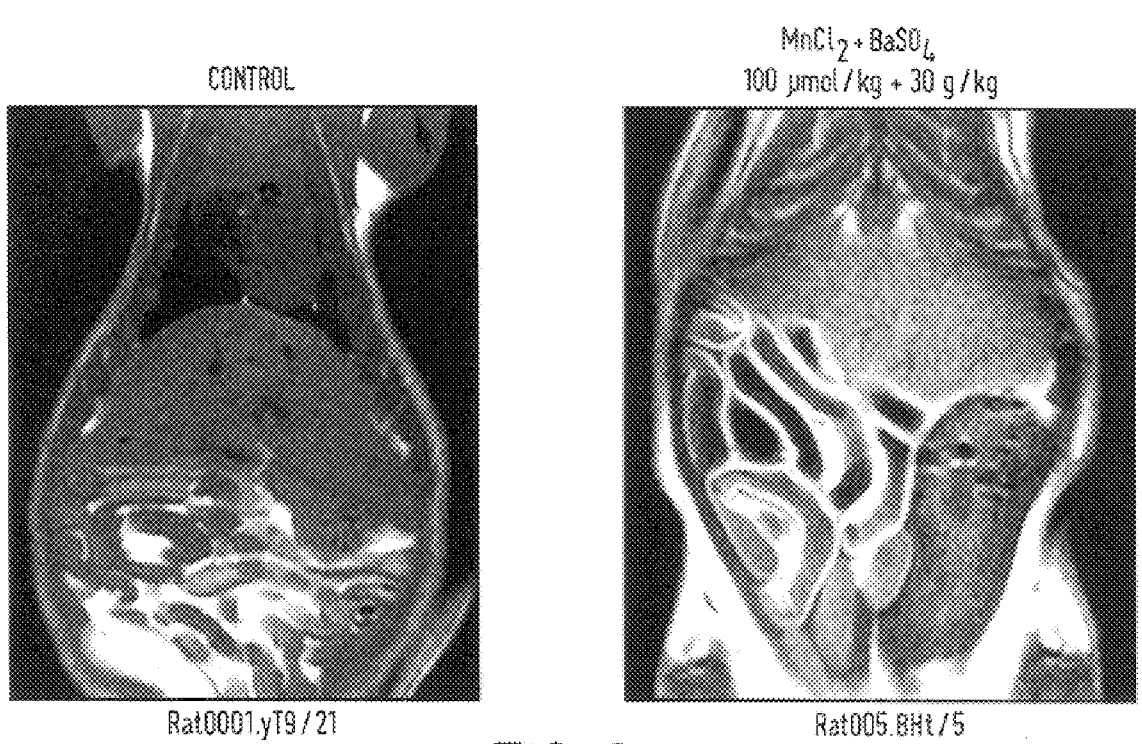
FIG. 3 illustrates the effect of orally administered $MnCl_2$+$BaSO_4$®.

FIG. 3 illustrates the effect of orally administered $MnCl_2$ (100 μmol/kg)+$BaSO_4$ (30 g/kg) on signal intensity of coronal $T_1$-weighted spin-echo images (TR/TE=120/12 ms) 2 hours after administration in fasted (18 hours) rats. $BaSO_4$ was administered three times, at 0, 30 and 60 min after administration of $MnCl_2$. The strong enhancement of the signal intensity of the liver and the intestinal wall is to be noted.

Figure 4:
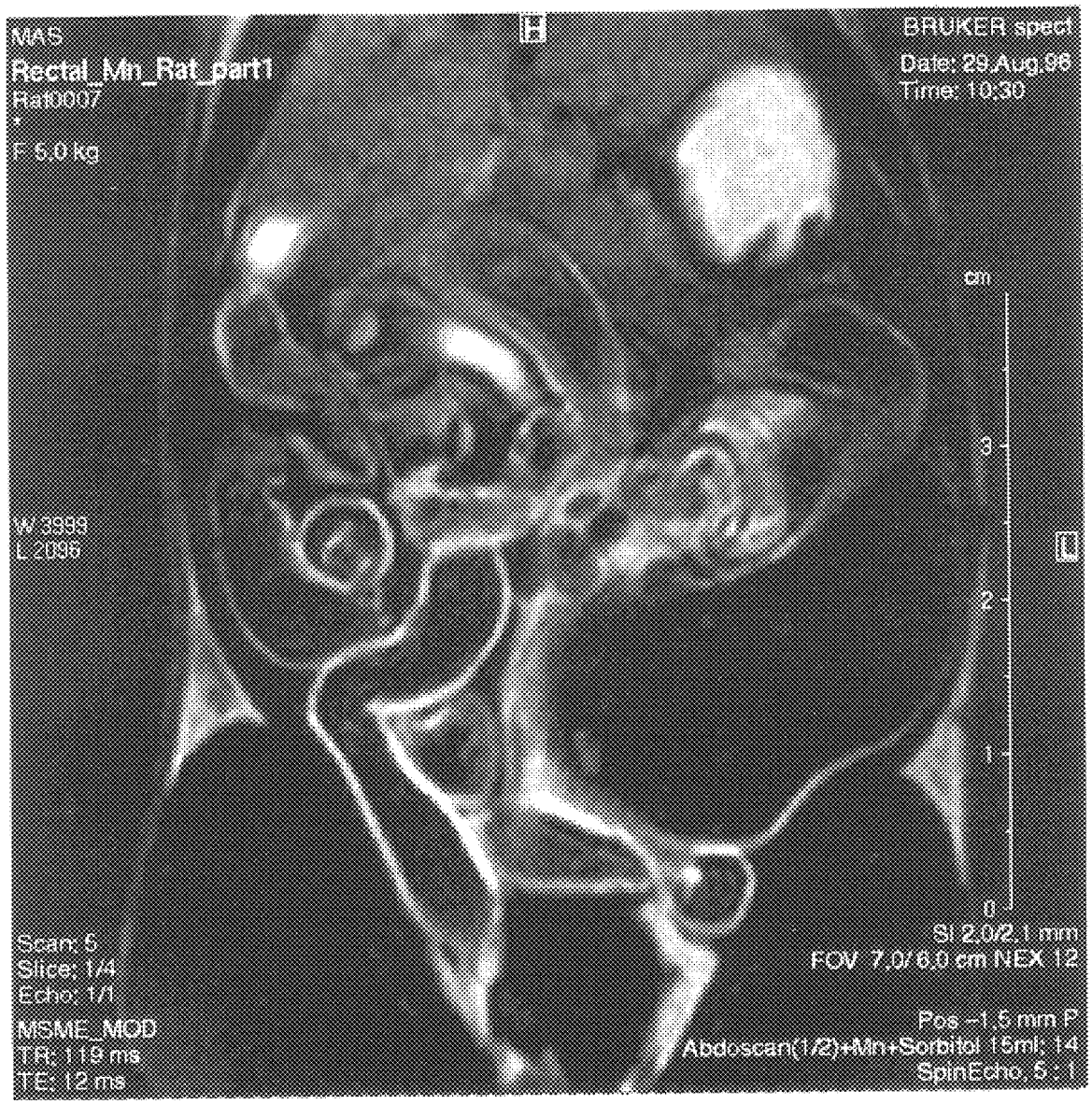
FIG. 4 illustrates the effect of rectally administered $MnCl_2$+Abdoscan®.

FIG. 4 illustrates the effect of rectally administered $MnCl_2$ (100 μmol/kg)+Abdoscan® (80 μmol Fe/kg)+sorbitol (2%) on signal intensity of coronal $T_1$-weighted spin-echo images (TR/TE=120/12 ms) 2.5 hours after administration in fasted (24 hours) rats. The strong enhancement of the signal intensity of the colon wall is to be noted.

What is claimed is:

1. A method of functional magnetic resonance imaging of a human or non-human animal body, which method comprises administering into the gastrointestinal tract of said body an effective amount of a composition comprising (a) a first contrast agent comprising a physiologically tolerable manganese compound or a salt thereof, together with (b) a second contrast agent, and generating a magnetic resonance image of the gastrointestinal tract of said body, thereby enabling discrimination between the functioning and non-functioning regions of the intestines.

2. A method of functional magnetic resonance imaging of a human or non-human animal body, which method comprises simultaneous, separate, or sequential administration into the gastrointestinal tract of said body an effective amount of a composition comprising (a) a physiologically tolerable manganese compound or a salt thereof, together with (b) a second contrast agent, and generating a magnetic resonance image of the gastrointestinal tract of said body, thereby enabling discrimination between the functioning and non-functioning regions of the intestines.

3. A method as claimed in claim 1 wherein said second contrast agent has a negative contrast effect.

4. A method as claimed in claim 1 wherein said second contrast agent is substantially retained within the gut during imaging.

5. A method as claimed in claim 1 wherein the manganese-containing contrast medium composition has a manganese concentration greater than 10 mM.

6. A method as claimed in claim 1 wherein the manganese-containing contrast medium composition has a manganese concentration of from 0.1 mM to 10 mM.

7. A method as claimed in claim 1 wherein said second contrast agent is selected from the group consisting of:
   (a) a particulate ferromagnetic or superparamagnetic material;
   (b) Gd or Dy ions bound to a polymeric matrix;
   (c) a gas, a gas containing agent or gas filled particles; and
   (d) insoluble barium compounds.

8. A method as claimed in claim 1 wherein said manganese compound is a chelate or salt in which the manganese is present as Mn(II).

9. A method as claimed in claim 1 wherein said manganese compound is selected from the group consisting of manganese chloride, manganese ascorbate, manganese kojate, manganese salicylate and manganese gluconate.

10. A method as claimed in claim 1 wherein said body has fasted for a period of at least 6 hours prior to enteral administration of said contrast medium composition or compositions.

11. A method as claimed in claim 10 wherein said body has fasted for a period of at least 10 hours prior to administration of said contrast medium composition or compositions.

12. A method as claimed in claim 1 wherein said contrast medium composition or compositions are rectally administered to the gastrointestinal tract of a human or non-human animal body which is substantially free from hydrophilic polymer components containing a significant amount of a $Mn^{2+}$-chelating unit at the time of imaging.

13. A method as claimed in claim 1 wherein said contrast medium composition or compositions are administered separately, prior to, during or subsequent to administration of an uptake promoter capable of enhancing manganese transport across the membranes of the gastrointestinal tract.

14. A method as claimed in claim 13 wherein said contrast medium composition or compositions are administered as a combined preparation with said uptake promoter.

15. A method as claimed in claim 13 wherein said uptake promoter comprises a physiologically tolerable reducing compound containing an a-hydroxy ketone group, a physiologically tolerable acid containing α- and/or β-hydroxy or amino groups, vitamin D, or a mixture thereof.

16. A method as claimed in claim 13 wherein said uptake promoter is selected from the group consisting of ascorbic acid, kojic acid, gluconic acid and salicylic acid.

17. A method as claimed in claim 13 wherein said uptake promoter comprises an α- or β-amino acid.

18. A method as claimed in claim 17 wherein said uptake promoter is selected from the group consisting of alanine, glycine, valine, glutamine, aspartic acid, glutamic acid, lysine, arginine, cysteine and methionine.

19. A method as claimed in claim 13 wherein the molar ratio of manganese to uptake promoter is from 1:0.2 to 1:50.

20. A method as claimed in claim 13 wherein the uptake promoter is present in whole or in part as the counterion to the manganese ions.

21. A method as claimed in claim 1 wherein said method of imaging is capable of generating a series of images with time intervals of less than 20 seconds.

22. A method as claimed in claim 1 wherein said method of imaging is a spin echo or gradient echo imaging procedure.

23. A method as claimed in claim 1 wherein said method of imaging is a spiral MR imaging technique.

24. A method as claimed in claim 1 which provides an image of the stomach, intestine, liver, bile duct or gall bladder of said body.

* * * * *